United States Patent [19]

Yu et al.

[11] Patent Number: 5,438,991
[45] Date of Patent: Aug. 8, 1995

[54] METHOD AND APPARATUS FOR CONTROLLING A RADIATION TREATMENT FIELD

[75] Inventors: Cedric Yu; John Wong, both of Bloomfield Hills, Mich.

[73] Assignee: William Beaumont Hospital, Royal Oak, Mich.

[21] Appl. No.: 137,568

[22] Filed: Oct. 18, 1993

[51] Int. Cl.$^6$ ............................................. A61B 6/00
[52] U.S. Cl. .............................. 128/653.1; 378/65; 378/151
[58] Field of Search ............... 128/653.1; 606/130; 378/65, 151

[56] References Cited

U.S. PATENT DOCUMENTS

| | | | |
|---|---|---|---|
| 5,207,223 | 5/1993 | Adler | 128/653.1 |
| 5,233,990 | 8/1993 | Barnea | 128/653.1 |
| 5,297,037 | 3/1994 | Ifuku | 378/65 X |

*Primary Examiner*—Ruth S. Smith
*Attorney, Agent, or Firm*—Harness, Dickey & Pierce

[57] ABSTRACT

A method and system for simulating and verifying a radiation therapy beam prior to treatment. The system also permits the accurate positioning of the beam with respect to the patient. The system utilizes a contour on a prescription image which defines the location and shape of a desired radiation treatment area to generate a transmissive projection which projects the exact field contour onto the patient during simulation. The patient can then be marked with this field contour prior to treatment in the simulation apparatus. With the patient placed in the treatment apparatus the accurate positioning of the patient can be achieved by aligning the patient's skin markings with a light projected through a multi-leaf collimator onto the skin. Furthermore, the correct functioning of the multi-leaf collimator can be verified in this manner since incorrect leaf positions will show up in the light projected onto the patient's skin. The transmissive projection means may comprise, in the preferred embodiment, a liquid crystal display projection device under control of a host computer storing a digitized image of the field contour.

12 Claims, 4 Drawing Sheets

METHOD AND APPARATUS FOR CONTROLLING A RADIATION TREATMENT FIELD

BACKGROUND OF THE INVENTION

1. Technical Field

This invention relates to radiation therapy, and more particularly to a method and apparatus for controlling and verifying the shape and location of a radiation beam during radiation therapy.

2. Discussion

Radiation therapy deals with the treatment of disease with ionizing radiation. The diseases most commonly treated in this manner are cancer and allied diseases. In cancer therapy the objective is to destroy a tumor without causing irreparable radiation damage in normal body tissues that must of necessity be irradiated in the process of delivering a lethal dose to the tumor. This applies particularly to important normal structures in the vicinity of the tumor. Thus, the relative radio-sensitivity of the tumor with respect to these normal structures is an important factor determining the success of the treatment.

The optimal differential between the effect on the tumor and the effect on normal tissues of the patient as a whole results from the proper adjustment of many treatment factors. The time factor is very important. This involves the administration of the therapeutic dose in one of three ways: by one short treatment; by protraction as continuous irradiation over a long time; or by fractionation in small repeated doses. The importance of the distribution of the radiation in the patient's body is obvious. Ideally, only the tumor should be irradiated but this is normally impossible, because in general there is adjacent normal tissues overlaying or underlaying the tumor volume.

One technique for minimizing the exposure of normal tissue is to control the precise shape of the radiation beam. This can be done by simulating the radiation therapy in a simulator prior to actual radiation treatment. In one conventional technique, a patient is placed in a simulator and a light in the simulator simulates the rectangular beam shape of the radiation field on the patient. This beam axis location as well as field corners can then be drawn on the patient's skin to aid the set-up on radiation therapy apparatus. In addition, an X-ray can be taken of the target area on the patient while in the simulator. The desired field shape surrounding the tumor is then drawn (typically by hand) on the X-ray film. The X-ray film with the hand drawn field shape is then used to manufacture a set of field shaping blocks which are placed in a tray in the radiation therapy apparatus to control the shape of the radiation beam to the desired shape. For example, the blocks may be made of molded cerrobend. When the patient is placed in the radiation therapy apparatus, the rectangular field shape markings on the patient can be lined up with a field shape light simulating the actual beam position. Then, the blocks conforming to the particular desired field shape are installed and the radiation beam is administered.

One problem with this conventional technique is the length of time that it takes to produce the (cerrobend) blocks, which is usually a matter of hours or days. Storage of the bulky blocks is also a problem. Another problem with this technique is that only the rectangular field shape is drawn on the patient and verified in the treatment machine, but not the actual irregular field shape. This limits the accuracy of positioning of the patient with respect to the desired field. One approach sometimes used to overcome this particular limitation is to return the patient to the simulator after the cerrobend blocks are manufactured. With the blocks placed in the simulator the exact desired irregular field shape is then drawn on the patient. Then, when the patient is placed in the treatment apparatus, with the same blocks installed, the field projection light will project the field shape through the blocks onto the patient and by using the marks on the patient, the patient can be precisely positioned. However, while this approach improves accuracy, it increases rather than decreases the number of steps required to accomplish the desired treatment.

An alternative approach to controlling the radiation beam which is gaining wide acceptance is the use a device known as a multi-leaf collimator. The multi-leaf collimator consists of opposing arrays of narrow tungsten leaves placed in front of the radiation beam. By driving each leaf into different positions, virtually any desired field shape can be achieved in radiation therapy. It is expected that all new medical linear accelerators will eventually include multi-leaf collimators.

A major drawback with the use of multi-leaf collimators is that there is no multi-leaf collimator on the simulator, and thus the field shape information cannot be drawn on the patient during simulation. Instead, the rectangular beam shape is the only useful shape that can be drawn on the patient. As a result, without additional marks, it is difficult to align the patient and treatment beam correctly for the radiation treatment. One obvious approach to solve this problem would be to use the a multi-leaf collimator inside the simulator. However, the complexity and cost of the multi-leaf collimator generally prevents such an approach. While less expensive simulator multi-leaf collimators using plastic leaves have been proposed, the cost and complexity of such an apparatus still are considered prohibitive for use in simulation.

Another problem with the multi-leaf collimator systems is the inability to verify the correct leaf position just prior to treatment. That is, there is currently no way to insure that all of the leaves are properly functioning and in proper position because there is not an effective technique for marking the actual field shape on the patient's skin with multi-leaf collimator systems. One possible way to do this is to transmit a low dose radiation test beam through the collimator and patient onto an X-ray filter. Unfortunately, the low dosage of the test beam results in an unclear image which does not permit accurate positioning of the patient and/or beam.

Thus, it would be desirable to provide a means for improving the positioning and verification of beam shape and location in radiation therapy. It would also be desirable to provide such a system which can provide accurate verification of beam position that requires only a single visit by the patient. Further, it would be desirable to provide a method for simulating beam shape and placement which is compatible with multi-leaf collimator systems. It would also be desirable to provide such a system which provides for the marking of the actual beam treatment pattern on the skin of the patient and which also is compatible with multi-leaf collimator systems. Also it would be desirable to provide a system which can verify the correct leaf placement in a multi-leaf collimator system.

SUMMARY OF THE INVENTION

Pursuant to the present invention, there is provided a method and system for simulating and verifying a radiation therapy beam prior to treatment. In accordance with a first aspect of the present invention a method of performing radiation treatment begins with the step of positioning the patient on a simulation apparatus. A radiological image of the treatment region of the patient is generated and a contour is prescribed on the radiological image which defines the location and shape of the desired radiation treatment area. A contour defining this shape is then input into a host computer and signals defining this contour are transmitted to a transmissive projection unit so that the signals produce the outline of the curve on the transmissive projection unit. Light is then projected through the transmissive projection unit onto the treatment area of the patient and the patient's skin marked to define the curve. Next, the patient is positioned on the radiation therapy apparatus, and light is projected through the radiation therapy apparatus onto the patient to verify that it correctly lines up with the marked curve on the patient.

In accordance with a second aspect of the present invention a system for marking a radiation treatment curve on a patient prior to radiation therapy is provided. This system includes a simulation apparatus which includes an X-ray apparatus for generating an X-ray image of a region of the patient. This system also includes a module for inputting into a host computer a desired radiation treatment area curve defined on the X-ray apparatus. A projection display unit is coupled to the host computer for generating a projection image having transmissive areas corresponding to the treatment curve in response to signals received from the host computer. Also, a light projection means is disposed in the simulator for projecting light through the projection display unit onto the treatment area of the patient. This light allows the treatment curve to be projected onto the patient. Thus, this patient's skin can be marked with the outline of the curve. This curve on the skin can then later be used in conjunction with the radiation treatment equipment to verify the correct positioning and functioning of the radiation treatment equipment.

In accordance with a third aspect of the present invention a method of marking a treatment curve on a patient prior to radiation therapy is provided. The method includes the steps of generating a radiological image of a region of a patient in a simulator. Next, a curve on the radiological image defining the location and shape of a desired radiation treatment area is produced. The curve is then reproduced on a transmissive surface with a radio-opaque ink. Next, light is projected through the transmissive surface onto a treatment area of the patient and the patient's skin is marked to define the treatment area.

The above described method and technique can provide accurate positioning and verification of radiation treatment areas on patients in a single visit without the necessity of manufacturing radiation blocks. Further, the present invention provides a quick and efficient way to simulate the actual radiation field contour on a patient prior to treatment in systems where multi-leaf collimators are used. Furthermore, the present invention allows the marking of the radiation treatment area on the patient which can be used to verify the position and correct functioning of a multi-leaf collimator system prior to radiation treatment.

BRIEF DESCRIPTION OF THE DRAWINGS

The various advantages of the present invention will become apparent to one skilled in the art by reading the following specification and by reference to the following drawings in which.

DETAILED DESCRIPTION OF THE PREFERRED EMBODIMENTS

Figure 1:
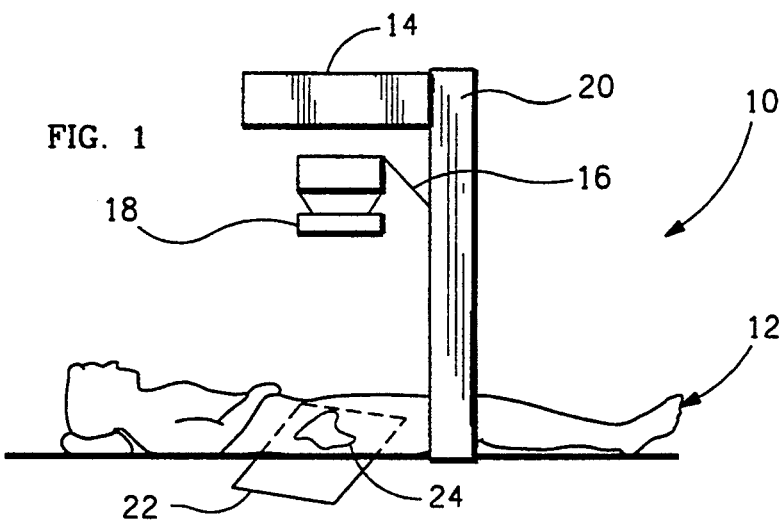
FIG. 1 is a diagram of a simulation apparatus used to mark a radiation treatment field contour on a patient in accordance with the present invention.

Referring now to FIG. 1 a simulation apparatus 10 used to simulate a radiation treatment on a patient 12 is shown. The simulation apparatus 10 includes an X-ray machine 14, a simulator light projector 16, a projection tray 18 and a mounting stand 20. As discussed above, in accordance with the prior art, prior to the use of multi-leaf collimators, a simulation apparatus 10 as shown in FIG. 1 was utilized by first taking an X-ray image of the treatment region of the patient. The X-ray film 22 thereby obtained could then have a desired treatment field contour drawn directly upon it, for example, by a prescribing physician. This X-ray film 22 containing the desired contour would then be used to manufacture cerrobend blocks containing an opening conforming to the desired contour. The blocks could then be used in a radiation treatment machine to block the radiation field in the desired manner producing a treatment field conforming to the desired contour. In accordance with that technique, the light projector 16 in the simulation apparatus could be used to project a rectangular field beam shape onto the patient. This shape could then be marked on the patient's skin and when the patient is later placed in the radiation treatment apparatus, this marking could be used to line up the patient with the general rectangular radiation beam position. However, the exact location of the contour was not marked on the patient and could not be confirmed.

In accordance with another prior art technique, the cerrobend blocks, once produced, would be placed in the tray 18 of the simulator 10 and the patient returned to the simulator. The projector light 16 would then project the field contour shape 23 directly onto the patient's skin. This contour could then be marked on the skin and used later when the patient is in the treatment machine to verify the exact location of the treatment contour prior to radiation treatment. Unfortunately, this technique requires a return visit to the simulator by the patient. Additional X-ray films normally are required to ensure the set-up reproduces that of the first visit prior to marking the field contour on the patient. The added time and cost was found to be unacceptable in most circumstances.

More recently, multi-leaf collimator systems have been employed. Multi-leaf collimators eliminate the necessity of the cerrobend blocks. However, the multi-leaf collimator, since it is not present in the simulator, cannot be used to draw a field contour onto the patient. In accordance with the present invention a system and method has been provided for allowing the marking of an exact field contour onto a patient in conjunction with the use of a multi-leaf collimator.

Figure 2:
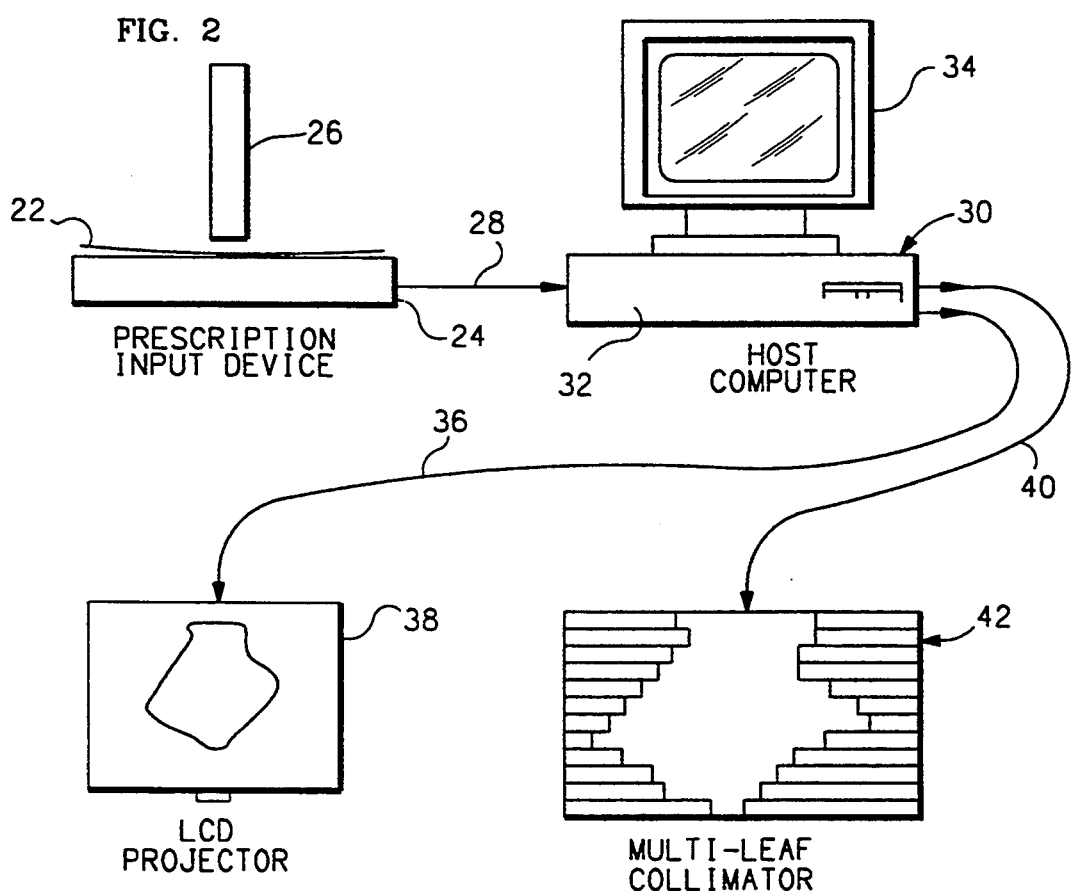
FIG. 2 is a diagram of the apparatus used to generate a field contour projection in accordance with the present invention.

In particular in accordance with one embodiment of the present invention, once an X-ray image 22 is generated in a simulator 10, the desired field contour is drawn onto the film 22 in a conventional manner. Referring to FIG. 2, this film 22 is then placed on a prescription input device 24. For example, this may comprise an optical scanner system which includes an optical reader unit 26 which digitizes the field contour 23 on the film 22. For example, the prescription input device 24 may comprise a conventional digitizer. The digitized contour information is then transmitted by the prescription input device 24 along line 28 to a host computer 30 which may comprise, for example, a PC having a CPU 32, a CRT display screen-34 and a keyboard (not shown). Host computer 30 may comprise a dedicated host computer for providing the digitized field Contour signals. Alternatively, as shown in FIG. 2 the same host computer used to control the multi-leaf collimator system may be used for this host computer 30. In any event, host computer 30 generates appropriate signals along output line 36 to drive a liquid crystal display (LCD) projector 38. The LCD panel contains a matrix of picture elements (pixels) which can be turned to a different shade of gray by switching on the pixel and applying different electric voltage levels on the pixel.

For example, the LCD projector 38 may comprise a modified LCD portable computer screen or may comprise an LCD display designed to be used with a conventional overhead projector such as the "EGA Data Display" available from Global Computer Supplies of Addison, Ill. In a similar manner the host computer 30 transmits signals along line 40 to a multi-leaf collimator 42 to produce the desired field contour as shown in FIG. 2. It should be noted that since the same input is used, the shape generated by the host computer 30 in the LCD projector 38 is the same as that in the multi-leaf collimator 42.

It should be noted that in order for the LCD projector 38 to give a field contour which matches the multi-leaf collimator in size, the source-to-LCD distance, source to the prescription image receptor distance, and the LCD pixel size must be taken into consideration. The magnification factor of the field shape size on the LCD to that on the prescription image film can be calculated by:

$$M_{LCD\text{-}to\text{-}film} = \frac{\text{Source-to-film distance}}{\text{Source-to-LCD distance}}$$

Since the existing field projection light 16 in the simulator has the same divergence as the radiation beam, the field shape, with the proper magnification displayed on the LCD will reflect the radiation field shapes of the radiation treatment machine. In more detail, referring to FIG. 3, the light source 16 in the simulator 10 originates at a point 44. The distance from this point LCD of projector 38 (mounted, in an LCD tray (not shown)) is designated as "a". The distance from the LCD projector 38 to the film 22 (or the patient's 12 skin) is designated as "b".) Thus, the magnification of the LCD-to-film is $$M = \frac{a + b}{a}$$

Figure 3:
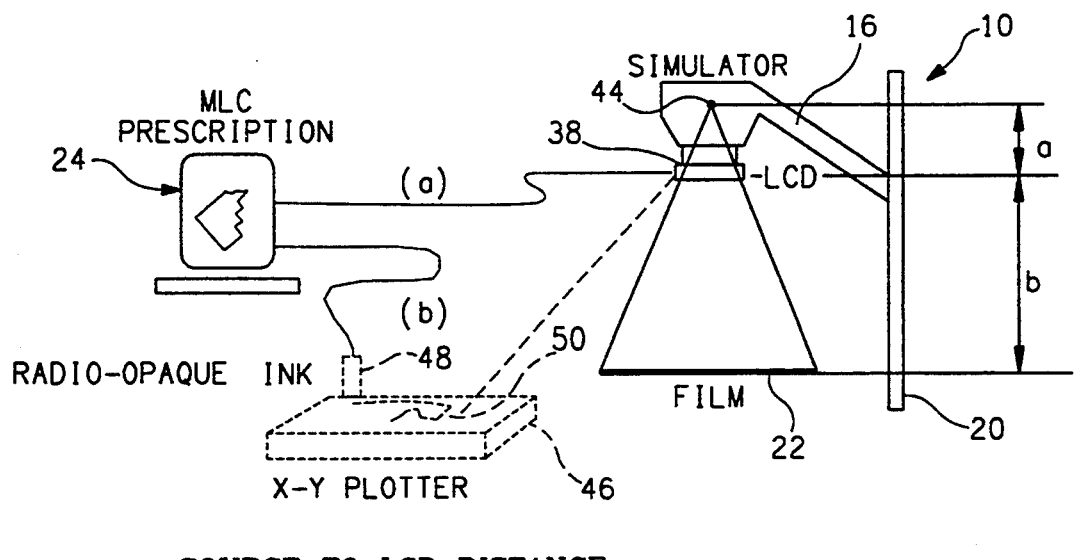
FIG. 3 is a diagram of an apparatus for generating a field contour projection utilizing a radio-opaque ink in accordance with another embodiment of the present invention.

Therefore the size of the field contour on the LCD is the size of the field contour on the film divided by M. Also, shown in FIG. 3 is an alternative embodiment of the present invention wherein an x/y plotter 46 is connected to the prescription input device 24 to thereby permit a radio-opaque ink pen 48 to draw the contour onto a transmissive film 50. In accordance with this embodiment, the film 50 with the radio-opaque field contour on it is placed in the tray in place of the LCD projector 38 under the simulator light unit 16. The effect of the film 50 with the radio-opaque ink field contour line will be the same as the LCD panel: the field contour can be projected on the patient. Additional verification can be provided by taking an X-ray. The field contour can then be shown on a new film, which can be used to compare with the prescription film.

Referring again to FIG. 1, once the desired field contour is drawn on the film 22, digitized by the prescription input device 24 and transmitted to the host computer 30, the LCD projector 38 (or the radio-opaque inked film 50) is placed in the simulator tray 18. The whole procedure normally takes only 3-5 minutes. The patient, whom has not been moved from the simulation apparatus, is then placed under the simulator light 16. In case longer time is needed for the physician to decide the prescription field, the patient can be moved from the simulation device. Placement of the patient in the precise location for field contour marking he/she was in when the film 22 was originally made, can be facilitated by the use of a rectangular field shape drawn on the patient's skin at the time the original radiological image 22 is made. Thus, before the LCD projector 38 or radio-opaque ink film 50 is placed in the tray 18, this rectangular shape can be projected by the simulator light 16 onto the patient's skin and the patient positioned so that this rectangular beam lines up with the rectangular skin markings, in cases where longer time is needed for the field contour to be generated.

Once this is done, and the LCD projector 38 (or radio-opaque film 50) is placed into the tray 18, the field contour 23 will be projected onto the patient's skin. This contour is then marked onto the patient's skin using convention skin marking techniques. With the exact field contour lines marked on the patient, it is a relatively simple matter to align the patient with the treatment beam on the treatment machine.

Figure 4:
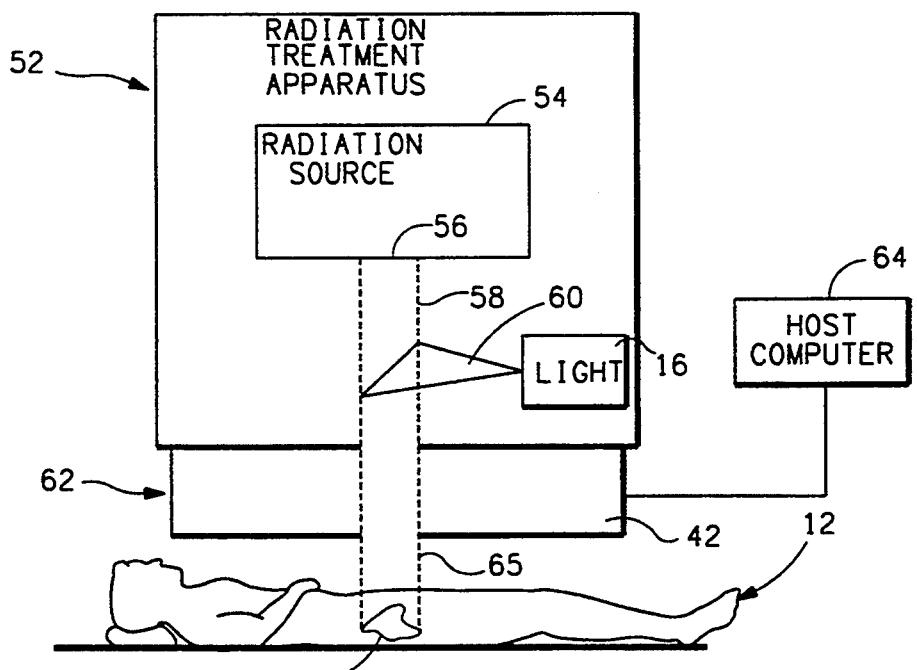
FIG. 4 is a diagram of a radiation treatment apparatus in accordance with the present invention.

Referring now to FIG. 4, a radiation treatment apparatus 52 is shown. This apparatus comprises a radiation source 54 which may comprise, for example, a linear accelerator having an opening 56 from which a radiation beam 58 exits. Also included in this apparatus is a light projection apparatus 60 similar to the light projection apparatus 16 shown in FIG. 1. Also shown in FIG. 4 is a multi-leaf collimator system 62 which includes a multi-leaf collimator 42 and a host computer 64. The multi-leaf collimator 42 under control of the host computer 64 generates the desired field contour as shown in more detail in FIG. 2.

During radiation treatment the radiation source 54 produces a beam of radiation 58 which passes through the opening 65 in the multi-leaf collimator 42 onto the patient 12. As discussed above, up to now, there had not been a way to verify the exact position of the field contour on the patient 12 with multi-leaf collimator systems 62. Instead, only the beam center projected by the light projector 60 on the patient could be verified.

In accordance with the present invention, however, the exact field contour 23 is drawn on the patient's skin while the patient was in the simulator 10 as described in more detail above. Thus, the patient can now be precisely positioned in the treatment apparatus 52 by projecting light from the light projector 60 through the multi-leaf collimator opening 65 to ensure that field contour 23 of the light generated by the light projector 60 matches that of the field contour 23 drawn on the patient 12. Of course, if it does not, the patient can be repositioned until it does.

If repositioning still does not produce a match between the projected light and the contour lines drawn on the patient, a malfunctioning leaf in the multi-leaf collimator 42 may be indicated. This points out another important advantage of the present invention, which is the verification of the proper functioning of the multi-leaf collimator 42. In prior uses of the multi-leaf collimator, there was not a precise visual verification that all of the leaves in the collimator 42 42 were functioning correctly. Thus, in addition to providing a means for precise positioning of the patient with respect to the desired field contour with a multi-leaf collimator system 62, the present invention provides an easy way to verify that all of the collimator leaves are where they should be just prior to radiation treatment. It should be noted as discussed above, a measure of verification was possible, prior to the present invention by utilizing a single shot low dose radiation beam into the treatment area and recording this dose on a X-ray film. However, the low dosage of this one shot beam resulted in relatively fuzzy X-ray images and all but the more gross malfunctions of the multi-leaf collimator 42 would not be detected using this method.

Figure 5:
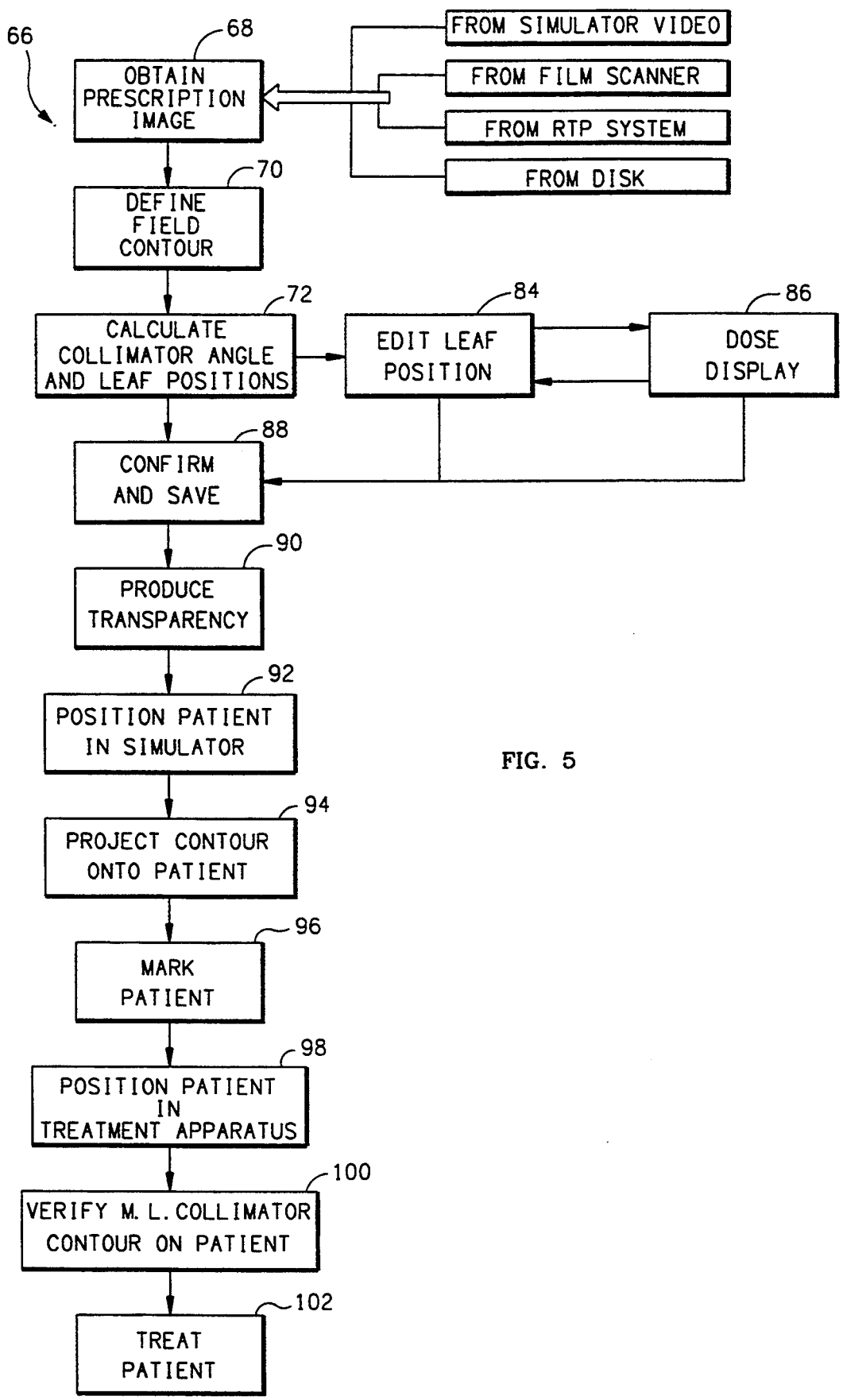
FIG. 5 is a system flow chart of a method of performing radiation treatment in accordance with the present invention.

Referring now to FIG. 5, a system flow chart 66 summarizes the method for controlling a radiation field in accordance with the present invention. In the first step 68 the prescription image is obtained. This image may be derived from the simulator X-ray apparatus 14, from the image intensifier video signal on the simulator, from a film scanner such as the Truvel, from a Radiation Treatment Planning (RTP) system, or previously stored disks. For example, as described above in FIG. 1 this prescription image may comprise the X-ray film 22. In step 70 the field contour is defined. Typically this will be done by hand by a physician after studying the prescription image and other available information regarding the tumor to be treated. It will be appreciated that while in the above embodiment described in connection with FIG. 3, an X/Y plotter was used to automatically draw the field contour on the transparency with radio-opaque ink, in an additional alternative embodiment, in some circumstances it may be possible to have the physician draw the field contour by hand with radio-opaque ink in step 70. In that case the prescription image film with the field contour drawn by hand with radio-opaque ink could then be used directly in the tray 18 for simulation as described above.

In any event, once the field contour is defined, the collimator angle and leaf positions are calculated in step 72. In step 84 the leaf positions are edited and in step 86 the dosages are displayed. A certain percentage of dose has to cover the tumor volume, based on the dose display, the leaf positions can be adjusted (edited) such that the prescribed dose coverage is achieved. A couple of iterations of leaf editing and dose display may be needed before the leaf positions are finalized.

Once the leaf positions are edited these positions are confirmed and saved. (These steps are accomplished using the computer 30) Next, in step 90 the transparency is produced either by use of the LCD projector 38 or by the x/y radio-opaque ink plotter 46. If the patient has been moved from the simulator, then in step 92 the patient is repositioned in the simulator apparatus 10, as described above in connection with FIG. 4. In step 94 the field contour is projected onto the skin of the patient and in step 96 the patient's skin is marked. Once marked, the patient can be scheduled for radiation treatment. For the treatment, the patient is positioned in the treatment apparatus 52, step 98 and the patient can be correctly aligned by matching the contour markings on the skin with the light from the projector 60 in the treatment apparatus 52 which passes through the multi-leaf collimator 42 which is conformed to the field contour. In step 100 the collimator contour is verified using the markings on the patient to insure that all of the leafs are correctly operating in the multi-leaf collimator. Finally, the patient is treated with radiation in step 102 using conventional treatment procedures.

Figure 7:
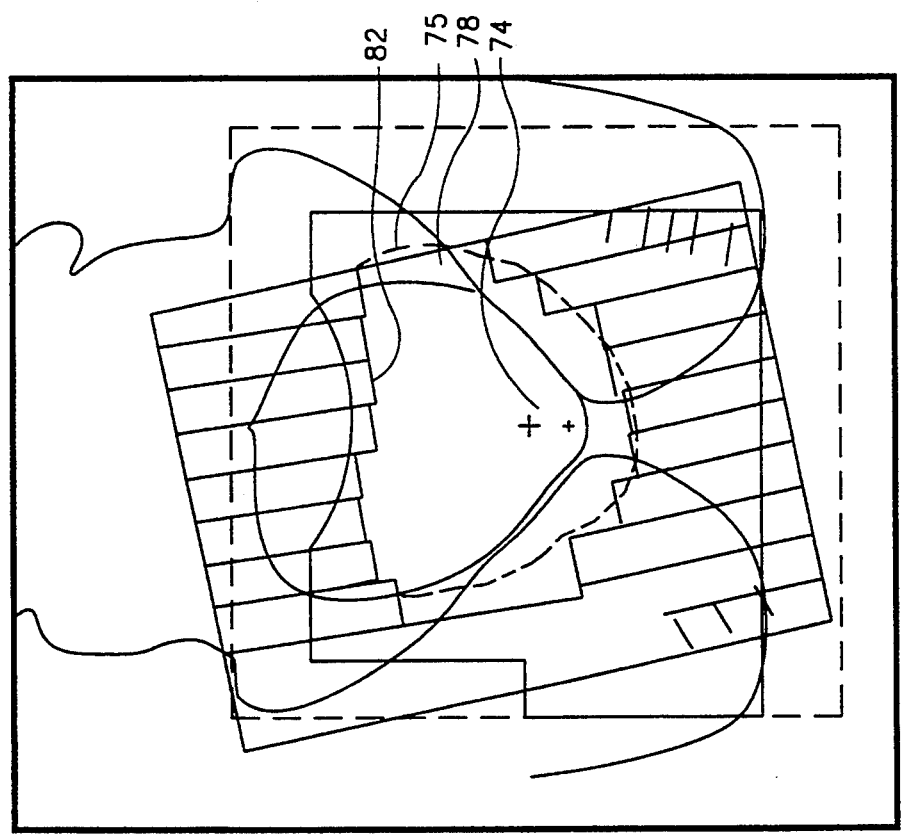
FIG. 7 is another example of a field contoured prescription in accordance with the present invention.
Figure 6:
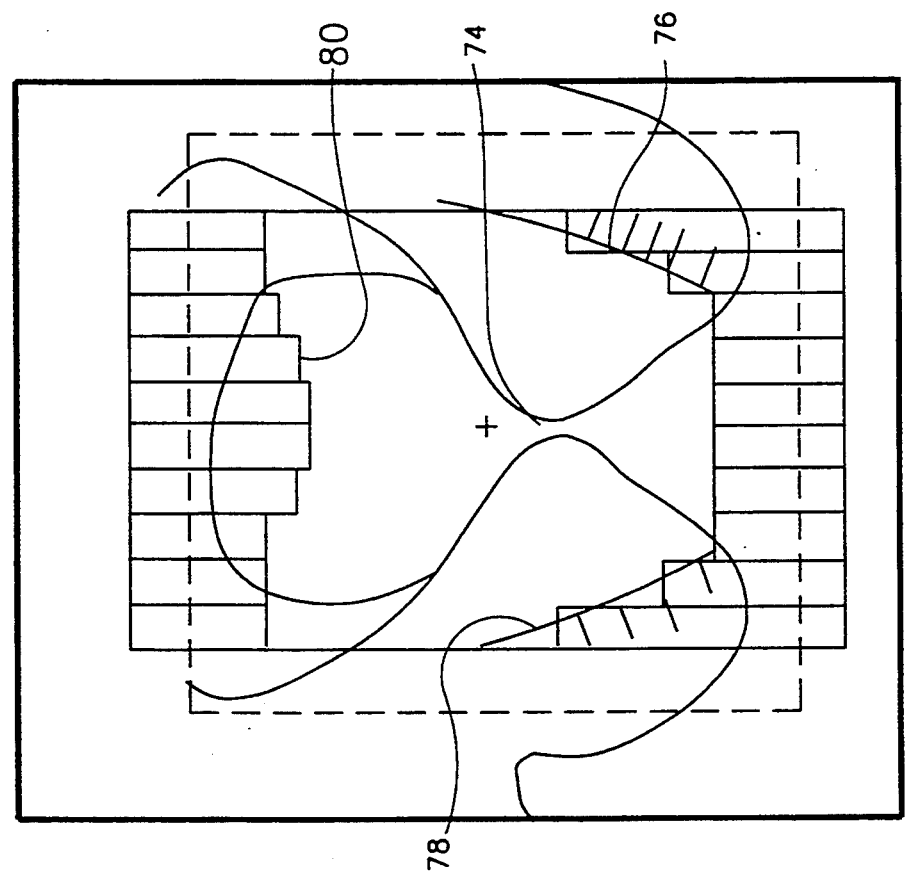
FIG. 6 is an example of a field contour prescription in accordance with the present invention.

Referring now to FIGS. 6 and 7 there are shown two radiological views of a prescription image. FIG. 7 has a desired field contour 75 drawn on it. Also shown in FIGS. 6 and 7 are the estimated leaf positions for both a large field as shown in FIG. 6 and a local boost field as shown in FIG. 7. In more detail, in FIG. 6 a pelvic field cancer treatment is shown including a tumor area 74, large field contour 76, local boost field contour 78 and multi-leaf collimator conformed field contours 80 and 82.

As described above, the present invention provides a method and apparatus for improving the positioning and verification of beam location and shape in radiation therapy. The system provides accurate verification that requires only a single visit to the treatment facility by the patient. Further, the present invention is compatible with multi-leaf collimator systems and provides for the marking of the actual treatment beam pattern on the skin of the patient when multi-leaf collimator systems are used. Also, the present invention provides a means for verifying the correct leaf placement on a multi-leaf collimator prior to radiation treatment. Those skilled in the art can appreciate that other advantages can be obtained from the use of this invention and that modification may be made without departing from the true spirit of the invention after studying the specification, drawings and following claims.

What is claimed is:

1. A method of performing radiation treatment on a patient, the method comprising the steps of:

positioning the patient on a simulation apparatus;

generating a radiological image of a region of the patient;

producing a curve on the radiological image defining the location and shape of a desired radiation treatment area;

inputting said curve into a host computer;

transmitting signals defining said curve from the host computer to a transmissive projection means operable to receive the signals and produce the outline of said curve on the transmissive projection means;

projecting light through the transmissive projection means to project the outline of said curve onto the treatment area of the patient;

marking the patient's skin to define the treatment area;

positioning the patient on a radiation therapy apparatus; and transmitting a radiation therapy beam from said radiation therapy apparatus onto said patient so that the radiation therapy beam conforms to the curve marked on said patient.

2. The method of claim 1 wherein said radiation therapy apparatus includes a multi-leaf collimator and the method includes the step of transmitting signals defining said curve from said host computer to the multi-leaf collimator, whereby the collimator openings will conform to said treatment region.

3. The method of claim 2 further comprising the step of projecting light through said multi-leaf collimator in said radiation therapy apparatus onto the marked area of the patient to verify that the multi-leaf collimator is producing the same shaped treatment region as marked on the patient, and also to verify that the patient is correctly positioned.

4. The method of claim 1 wherein the said step of taking a radiological image includes the step of taking an X-ray image.

5. The method of claim 1 wherein the step of producing a curve on the radiological image includes the step of manually drawing said curve on said radiological image.

6. The method of claim 1 wherein the step of inputting said curve into a host computer further comprises the step of digitizing said curve using a digitizer.

7. The method of claim 1 wherein the transmissive projection means comprises a liquid crystal display projection means operable to produce the outline of said curve, and wherein the step of transmitting includes the step of transmitting said signals to the liquid crystal display projection means to produce the outline of said curve.

8. The method of claim 1 wherein the transmissive projection means comprises a radio-opaque ink plotter having a transmissive film and wherein the step of transmitting includes the step of transmitting said signals to the radio-opaque ink plotter to produce the outline of said curve.

9. A system for marking a radiation treatment curve on a patient prior to radiation therapy, said system comprising:

a simulation apparatus including an X-ray apparatus for generating an X-ray image of a region of a patient;

a host computer;

means for inputting a radiation treatment area curve determined from an X-ray image into the host computer;

projection display means coupled to said host computer for generating a projection image having transmissive areas corresponding to said treatment curve in response to signals received from said host computer; and light projection means disposed in said simulation apparatus for projecting light through said projection display means onto the treatment area of the patient, wherein the treatment curve is projected onto the patient, namely on skin over the treatment area, and the patient skin is marked with the outline of said curve.

10. A system for performing radiation treatment on a patient, the system comprising:

a simulation apparatus including an X-ray apparatus for generating an X-ray image of a region of a patient;

a host computer;

means for inputting a radiation treatment area curve determined from the X-ray image which defines a radiation treatment area into said host computer;

projection display means coupled to said host computer for generating a projection image having transmissive areas corresponding to said treatment curve in response to signals received from said host computer;

light projection means disposed in said simulation apparatus for projecting light through said projection display means onto the treatment area of the patient, whereby the treatment curve is projected onto the patient, and the patient skin is marked with the outline of said curve;

radiation therapy apparatus including a multi-leaf collimator;

means for transmitting signals defining said treatment curve from said host computer to the multi-leaf collimator, whereby the collimator opening will conform to the treatment area;

means for projecting light through the multi-leaf collimator onto the marked area of said patient to verify that the multi-leaf collimator is producing the same shaped treatment area region as marked on the patient and also to verify that the patient is correctly positioned; and means for transmitting a radiation therapy beam through said multi-leaf collimator onto said patient, whereby the therapy beam conforms to the curve marked on said patient.

11. A method of marking a treatment curve on a patient prior to radiation therapy, said method comprising the steps of:

generating a radiological image of a region of a patient in a simulator;

producing a curve on the radiological image of a region of a patient in a simulator;

producing a curve on the radiological image defining the location and shape of a desired radiation treatment area;

reproducing said curve on a transmissive surface with a radio-opaque ink;

projecting fight through the transmissive surface onto the treatment area of the patient; and marking the patient's skin to define the treatment area.

12. A method of marking a treatment curve on a patient prior to radiation therapy, said method comprising the steps of:

generating a radiological image of a region of a patient in a simulator;

producing a curve on the radiological image of a region of a patient in a simulator;

producing a curve on the radiological image defining the location and shape of a desired radiation treatment area;

reproducing said curve on a transmissive surface with an LCD plate;

projecting light through the LCD plate onto the treatment area of the patient; and marking the patient's skin to define the treatment area.

* * * * *

UNITED STATES PATENT AND TRADEMARK OFFICE
CERTIFICATE OF CORRECTION

PATENT NO. : 5,438,991
DATED : August 8, 1995
INVENTOR(S) : Cedric Yu, et al.

It is certified that error appears in the above-indentified patent and that said Letters Patent is hereby corrected as shown below:

Column 10, Line 48, after "projecting" delete "fight" and insert --light--.

Signed and Sealed this

Twenty-sixth Day of December, 1995

Attest:

BRUCE LEHMAN

Attesting Officer

Commissioner of Patents and Trademarks